US009560968B2

(12) United States Patent
Lim et al.

(10) Patent No.: US 9,560,968 B2
(45) Date of Patent: Feb. 7, 2017

(54) REMOTE MONITORING FRAMEWORK

(71) Applicant: Nucleus Dynamics Pte. Ltd., Singapore (SG)

(72) Inventors: Kwang Yong Lim, Singapore (SG); Chin Hong Lim, Singapore (SG)

(73) Assignee: Nucleus Dynamics Pte. Ltd., Singapore (SG)

( * ) Notice: Subject to any disclaimer, the term of this patent is extended or adjusted under 35 U.S.C. 154(b) by 0 days.

(21) Appl. No.: 14/748,253

(22) Filed: Jun. 24, 2015

(65) Prior Publication Data

US 2015/0379735 A1 Dec. 31, 2015

Related U.S. Application Data

(60) Provisional application No. 62/017,853, filed on Jun. 27, 2014.

(51) Int. Cl.
*G06K 9/00* (2006.01)
*A61B 5/00* (2006.01)
*G06T 7/40* (2006.01)
*G06F 19/00* (2011.01)
*A61B 5/103* (2006.01)
*G06K 9/80* (2006.01)

(52) U.S. Cl.
CPC ........... *A61B 5/0013* (2013.01); *A61B 5/0002* (2013.01); *A61B 5/1032* (2013.01); *A61B 5/445* (2013.01); *G06F 19/321* (2013.01); *G06F 19/345* (2013.01); *G06T 7/408* (2013.01); *A61B 2576/00* (2013.01); *G06K 9/80* (2013.01); *G06T 2207/10024* (2013.01); *G06T 2207/30004* (2013.01)

(58) Field of Classification Search
CPC ........... G06T 7/408; G06T 2207/10024; G06T 2207/30004; G06K 9/80; A61B 2576/00; A61B 5/0002; A61B 5/0013; A61B 5/1032; A61B 5/445; G06F 19/321; G06F 19/345
USPC .................................................. 382/162, 165
See application file for complete search history.

(56) References Cited

U.S. PATENT DOCUMENTS

| 6,417,862 B1* | 7/2002 | Brothers | G06T 15/503 345/589 |
| 7,613,335 B2* | 11/2009 | McLennan | G06K 9/4652 382/128 |
| 7,972,266 B2* | 7/2011 | Gobeyn | A61B 3/113 348/222.1 |
| 8,423,080 B2* | 4/2013 | Linjama | G01J 3/02 356/425 |

(Continued)

OTHER PUBLICATIONS

M.A. Kevin Jensen et al., What accuracies can color sensors and mini-spectrometers achieve?, 2013, MAZeT Electronic Engineering & Manufacturing Services.

Primary Examiner — Kanjibhai Patel
(74) Attorney, Agent, or Firm — Horizon IP Pte. Ltd.

(57) ABSTRACT

Described herein is a technology for facilitating remote monitoring, in accordance with one aspect, image data and corresponding true color data of a region of interest is received by a computer system from a mobile device. The computer system may integrate the image data and the true color data to generate normalized true color data. The normalized true color data may then be mapped to device independent color image data. A recommendation may then be sent based on the device-independent color image data.

18 Claims, 4 Drawing Sheets

(56) References Cited

U.S. PATENT DOCUMENTS

| | | | |
|---|---|---|---|
| 9,179,045 B2* | 11/2015 | Qiao | H04N 1/6058 |
| 9,219,898 B2* | 12/2015 | Doser | G09G 5/02 |
| 2013/0250322 A1* | 9/2013 | Kawabata | H04N 1/60 |
| | | | 358/1.9 |

* cited by examiner

REMOTE MONITORING FRAMEWORK

CROSS-REFERENCE TO RELATED APPLICATION

This application claims the benefit of U.S. provisional application no. 62/017,853 filed on Jun. 27, 2014, the entire contents of which are incorporated herein by reference.

TECHNICAL FIELD

The present disclosure relates generally to a remote monitoring framework.

BACKGROUND

Currently, patients suffering from chronic wounds are typically cared for by a wound care nurse who may either assess wounds based on experience or use prohibitively expensive and specialized instruments to facilitate assessment. The wound care nurse may determine the stages of the wound based on a number of factors. Accurate determination of wound staging will impact the decision on which treatment to apply, and subsequently affect the rate of healing.

Since assessment of the wound staging is typically performed by wound care nurses, such assessment is subjected to wide variations based on their experience. Experienced wound care nurses may be able to effectively assess a wound and assign appropriate treatment for speedy recovery, while inexperienced nurses may apply less effective treatment due to inaccurate wound assessment, resulting in slower recovery. Shortage of experienced wound care nurses also means that these experienced wound care nurses are not able to take care of the increasing number of chronic wound patients.

SUMMARY

A computer-implemented technology for facilitating remote monitoring is described herein. In some implementations, image data and corresponding true color data of a region of interest is received by a computer system from a mobile device. The computer system may integrate the image data and the true color data to generate normalized true color data. The normalized true color data may then be mapped to device-independent color image data. A recommendation may then be sent based on the device-independent color image data.

With these and other advantages and features that will become hereinafter apparent, further information may be obtained by reference to the following detailed description and appended claims, and to the figures attached hereto.

BRIEF DESCRIPTION OF THE DRAWINGS

Some embodiments are illustrated in the accompanying figures. Like reference numerals in the figures designate like parts.

DETAILED DESCRIPTION

In the following description, for purposes of explanation, specific numbers, materials and configurations are set forth in order to provide a thorough understanding of the present frameworks and methods and in order to meet statutory written description, enablement, and best-mode requirements. However, it will be apparent to one skilled in the art that the present frameworks and methods may be practiced without the specific exemplary details. In other instances, well-known features are omitted or simplified to clarify the description of the exemplary implementations of present frameworks and methods, and to thereby better explain the present frameworks and methods. Furthermore, for ease of understanding, certain method steps are delineated as separate steps; however, these separately delineated steps should not be construed as necessarily order dependent or being separate in their performance.

Systems, methods, and apparatuses for facilitating remote monitoring are described herein. In one aspect of the present framework, a mobile device camera and a true color sensor are used to capture image data and true color data of a region of interest (e.g., wound) for remote assessment. The image data and true color data may be communicated to a remote server (e.g., cloud server) for assessment. The image data and true color data may be mapped to a true color space that advantageously models the nonlinear response of the human eye and is independent of device and ambient lighting. The processed image data may then be communicated to the caregiver, physician, clinician or other user for assessment. Such processed image data advantageously enables the user to assess an image as true to the real region of interest as possible. For example, the clinician can see the wound as if he or she is on-site tending to the wound for treatment, monitoring and/or diagnosis. These, and other exemplary features and advantages, will be discussed in more details in the following description.

For purposes of illustration, the present framework may be described in the context of remote monitoring of chronic wounds, such as those caused by injury, surgical operation, trauma, ulceration, etc. However, it should be appreciated that the present framework may also be applied to monitoring other types of regions of interest, such as medical diagnostic applications (e.g., skin diagnostics) as well as non-medical applications, such as those in the geophysical field, printing industry, interior design, textile coloring for fashion, vision inspection in manufacturing or production applications, white balance for photography, display calibration, and so forth.

Figure 1:
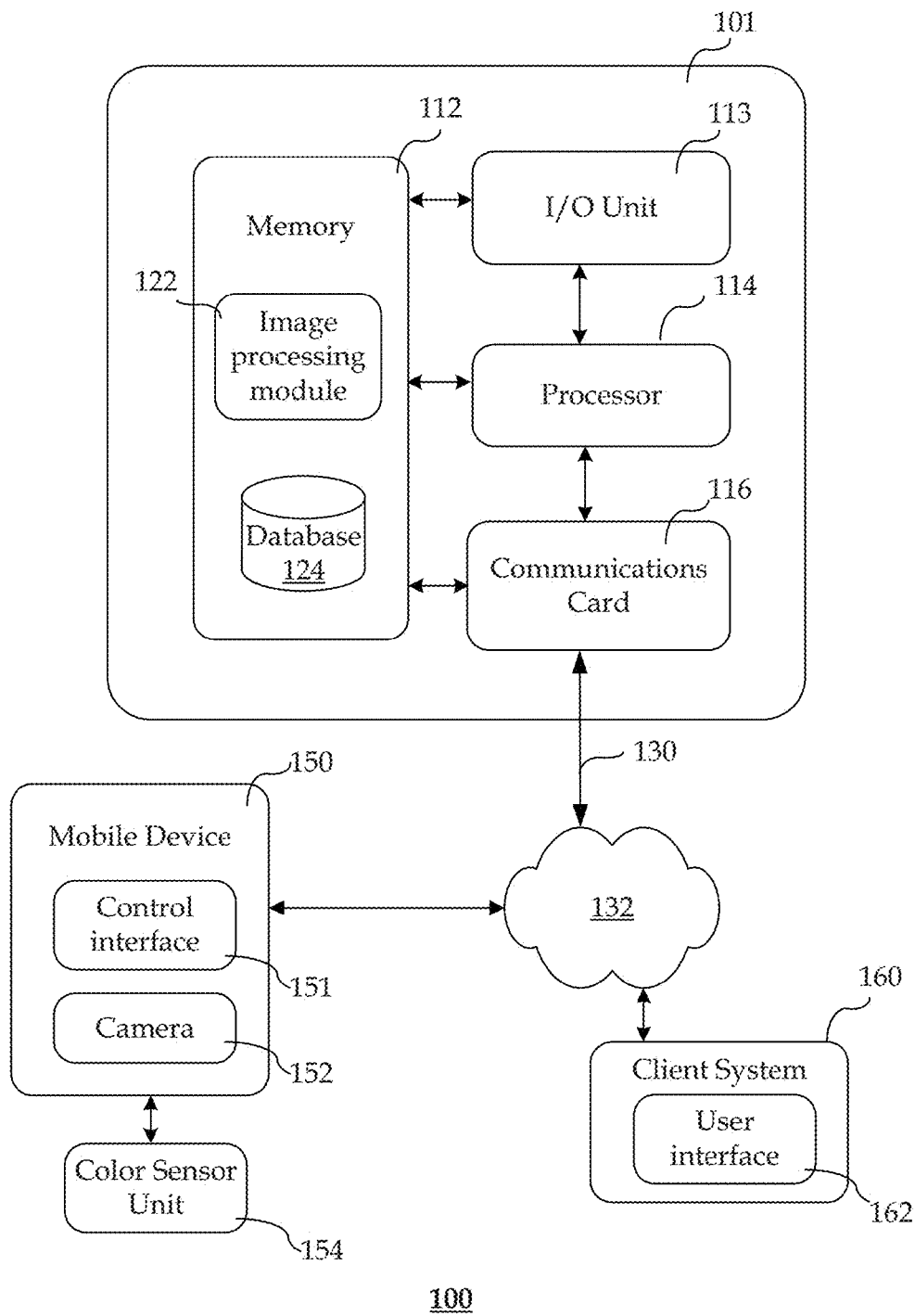
FIG. 1 is a block diagram illustrating an exemplary system.

FIG. 1 is a block diagram illustrating an exemplary system 100 that implements the framework described herein. The system 100 generally includes a server 101, a mobile device 150 and a client system 160, at least some of which are communicatively coupled through a network 132. Although shown as a single machine, the server 101 may include more than one server, such as a server pool or cloud computing providers. For example, the server 101 may be implemented as a cloud, delivering content or services (e.g., Software as a Service or Saas) to one or more applications (or Apps), devices and/or systems.

Turning to the server 101 in more detail, it may include, a non-transitory computer-readable media or memory 112, a processor 114, an input-output unit 113 and a communications card 116. Non-transitory computer-readable media or memory 112 may store machine-executable instructions, data, and various programs, such as an operating system (not shown), an image processing module 122 and a database 124 for implementing the techniques described herein, all of which may be executable by processor 114. As such, the server 101 is a general-purpose computer system that becomes a specific-purpose computer system when executing the machine-executable instructions. Alternatively, the image processing module 122 and/or database 124 described herein may be implemented as part of a software product or application, which is executed via the operating system. The application may be integrated into an existing software application, such as an add-on or plug-in to an existing application, or as a separate application. The existing software application may be a suite of software applications. It should be noted that the image processing module 122 and/or database 124 may be hosted in whole or in part by different computer systems in some implementations. Thus, the techniques described herein may occur locally on the server 101, or may occur in other computer systems and be reported to the server 101.

Each computer program may be implemented in a high-level procedural or object-oriented programming language, or in assembly or machine language if desired. The language may be a compiled or interpreted language. The machine-executable instructions are not intended to be limited to any particular programming language and implementation thereof. It will be appreciated that a variety of programming languages and coding thereof may be used to implement the teachings of the disclosure contained herein.

Generally, memory 112 may include any memory or database module for storing data and program instructions. Memory 112 may take the form of volatile or non-volatile memory including, without limitation, magnetic media, optical media, random access memory (RAM), read-only memory (ROM), removable media, or any other suitable local or remote memory component. Memory 112 may store various objects or data, including classes, frameworks, applications, backup data, business objects, jobs, web pages, web page templates, database tables, repositories storing business and/or dynamic information, and any other appropriate information including any parameters, variables, algorithms, instructions, rules, constraints, or references thereto associated with the purposes of the server 101.

In some implementations, server 101 is communicatively coupled to an input device (e.g., keyboard, touch screen or mouse) and a display device (e.g., monitor or screen) via the I/O unit 113. In addition, server 101 may also include other devices such as a communications card or device (e.g., a modem and/or a network adapter) for exchanging data with a network 132 using a communications link 130 (e.g., a telephone line, a wireless network link, a wired network link, or a cable network), and other support circuits (e.g., a cache, power supply, clock circuits, communications bus, etc.). In addition, any of the foregoing may be supplemented by, or incorporated in, application-specific integrated circuits.

Server 101 may operate in a networked environment using logical connections to one or more mobile devices 150 and client system 160 over one or more intermediate networks 132. These networks 132 generally represent any protocols, adapters, components, and other general infrastructure associated with wired and/or wireless communications networks. Such networks 132 may be global, regional, local, and/or personal in scope and nature, as appropriate in different implementations. The network 132 may be all or a portion of an enterprise or secured network, while in another instance, at least a portion of the network 132 may represent a connection to the Internet. In some instances, a portion of the network may be a virtual private network (VPN). The network 132 may communicate, for example, Internet Protocol (IP) packets, Frame Relay frames, Asynchronous Transfer Mode (ATM) cells, voice, video, data, and other suitable information between network addresses. The network 132 may also include one or more local area networks (LANs), radio access networks (RANs), metropolitan area networks (MANs), wide area networks (WANs), all or a portion of the World Wide Web (Internet), and/or any other communication system or systems at one or more locations.

In general, mobile device 150 may be any computing device operable to connect to or communicate with at least the server 101, the client system 160 and/or the network 132 using a wired or wireless connection. In some implementations, the mobile device 150 can be used by an end-user to communicate information using radio technology. The mobile device 150 may be a cellular phone, a personal data assistant (PDA), a smartphone, a laptop, a tablet personal computer (PC), an e-reader, a media player, a digital camera, a video camera, a Session Initiation Protocol (SIP) phone, a touch screen terminal, an enhanced general packet radio service (EGPRS) mobile phone, a navigation device, an email device, a game console, any other suitable wireless communication device capable of performing a plurality of tasks including communicating information using a radio technology, or a combination of any two or more of these devices.

The mobile device 150 may include an input device (e.g., keyboard, touchscreen, microphone, etc.), an output device (e.g., display screen, speaker, etc.), a processor, a memory or non-transitory computer-readable media, an interface card, and so forth. In some implementations, the memory stores a control interface 151. The control interface 151 may be, for example, a mobile application for App). The control interface 151 may be written in any programming language, such as C, C++, Java, Visual Basic, assembler, Perl, any suitable version of 4GL, as well as others.

Mobile device 150 may further include a camera 152 for acquiring image data of the region of interest. Such camera 152 may be integrated in the mobile device (e.g., smartphone) for capturing photographs and/or videos. Camera 152 typically includes a standard lens (e.g., fixed focus lens) and small image sensors (e.g., complementary metal oxide semiconductor or CMOS sensors) that limit their performance in poor lighting. The image data generated by camera 152 is device-dependent and adversely affected by poor ambient lighting conditions. The image data may be stored in any suitable file format, such as Joint Photographic Experts Group (JPEG or JPG), TIFF, Graphics Interchange Format (GIF), PNG, Raw, etc.

A color sensor unit 154 may be communicatively coupled or attached to mobile device 150 for acquiring true color data of the region of interest. The color sensor unit 154 may be communicatively coupled via, for example, an audio jack or universal serial bus (USB) connector inserted into the input channel of the mobile device 150. Alternatively, the color sensor unit 154 may be integrated in the mobile device 150. Other methods of coupling are also useful. True color data acquired by the color sensor unit 154 may be stored in the mobile device 150 and/or communicated to the server 101 via the control interface 151.

True color data represents the region of interest using a color model that accurately models the human perception of colors. One such color model is the Red Green Blue (RGB) color model, which is an additive color model in which red, green and blue light are added together in various ways to reproduce a broad array of colors. A large percentage of the visible spectrum (380 nm to 750 nm wavelength) can be reproduced using the RGB color model. RGB is a device-dependent color model. Different devices detect or reproduce a given RGB value differently, since the color elements (e.g., phosphors or dyes) and their response to the individual red, green and blue levels vary from manufacturer to manufacturer, or even in the same device over time. Therefore, an RGB value does not define the same color across devices without some kind of color management.

Figure 2:
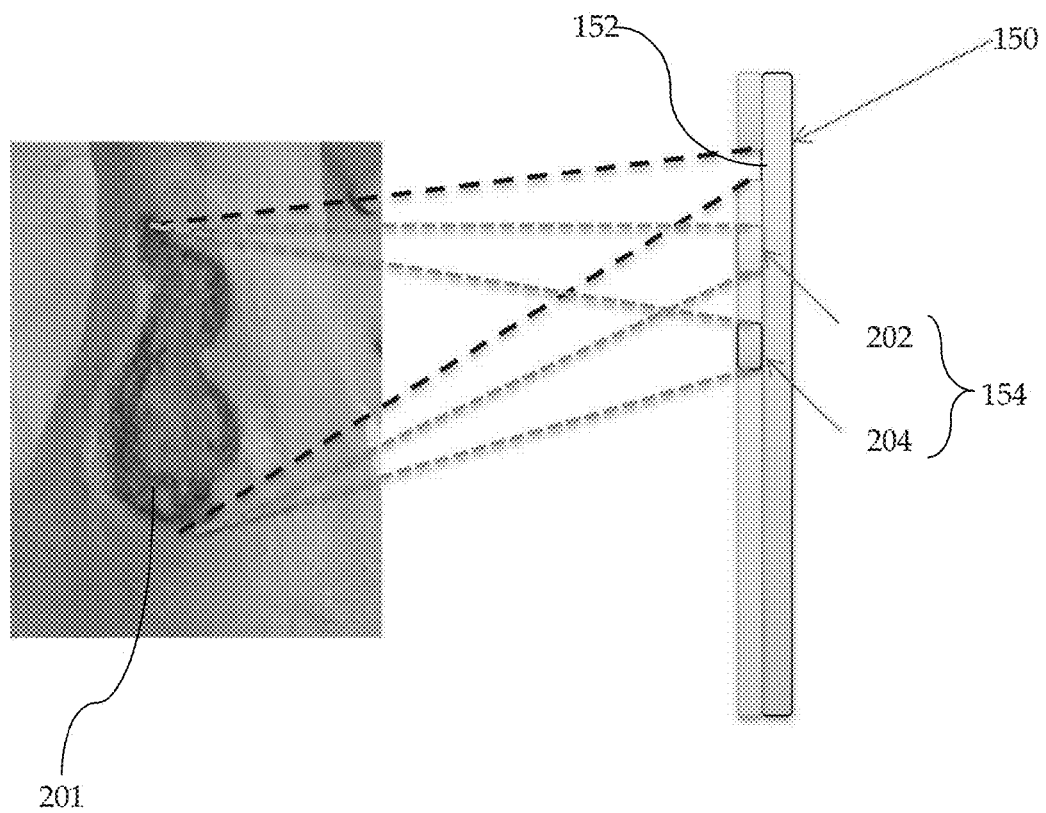
FIG. 2 shows an exemplary color sensor unit communicatively coupled to a mobile phone.

FIG. 2 shows an exemplary color sensor unit 154 communicatively coupled to the mobile phone 150 for acquiring true color data of a wound 201. In some implementations, the color sensor unit 154 includes a true color sensor 202 and a light source 204. True color sensor 202 performs similarly to a color spectrometer, and obtains a more accurate or true color response for pixels by distinguishing and measuring colors based on, for example, the RGB color model. True color sensor 202 may operate based on the tristimulus principle of color identification for precision colorimeters. The tristimulus method measures light emitted from the light source 204 and reflected from the wound using three color sensors packed in an area of a single pixel of the image sensor. These sensors may be filtered to invoke the same response to red, green and blue colors as the human eye.

Returning to FIG. 1, client system 160 may be any electronic computer devices operable to receive, transmit, process, and store any appropriate data associated with the system 100 of FIG. 1. Although shown as a single machine, client system 160 may be embodied as multiple machines. Client system 160 may be, for example, a smartphone, a mobile computing device, a personal computer, a desktop, a laptop, a touch screen terminal, a workstation, a network computer, a server, etc. The client system 160 may include one or more processors or any other suitable processing device, and typically includes many or all of the elements described above relative to server 101. Client system 160 may also include one or more instances of non-transitory computer readable storage media or memory devices (not shown).

The memory of client system 160 may include a user interface 162 suitable for interacting with the image processing module 122 and/or database 124 over the network 132. Client system 160 serves to facilitate the display and/or analysis of information related to the processed image data from server 101. For example, the user interface 162 may be used by a physician or other caregiver (e.g., nurse) to view the processed image data and make recommendations for remote wound management (e.g., treatment). These and other exemplary features will be described in more detail in the following description.

Figure 3:
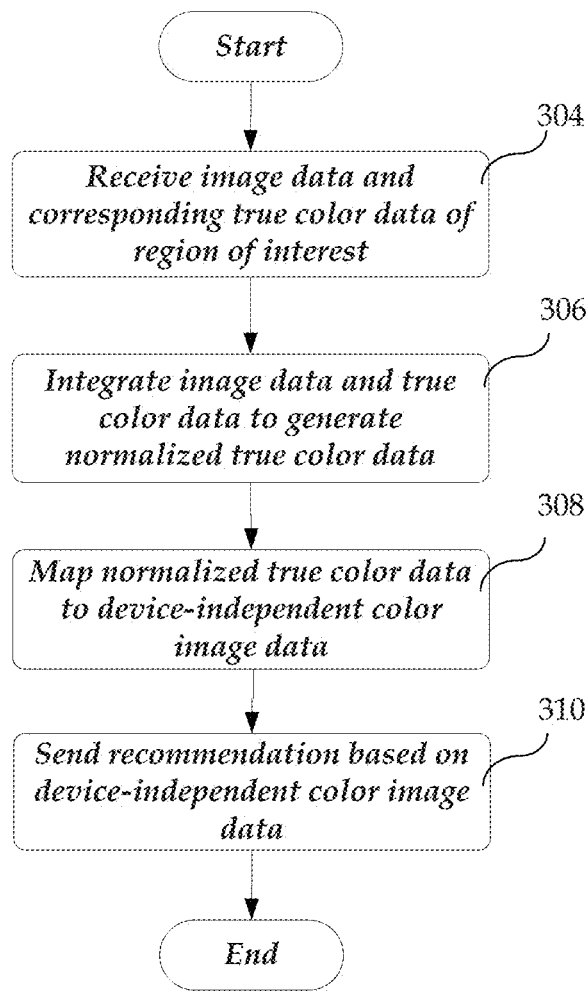
FIG. 3 shows an exemplary method of remote monitoring.

FIG. 3 shows an exemplary method 300 of remote monitoring. The method 300 may be implemented by the system 100, as previously described with reference to FIG. 1. It should be noted that in the following discussion, reference will be made, using like numerals, to the features described in FIG. 1.

At 304, image processing module 122 receives image data and corresponding true color data of a region of interest from mobile device 150. The region of interest may be, for example, a wound caused by injury, surgical operation, trauma, ulceration, etc., or any other type of region of interest that require monitoring. In some implementations, control interface 151 in mobile device 150 initiates the acquisition of image data and corresponding true color data of the region of interest. The acquisition may be performed in response to, for example, a user selection of a graphical user interface element (e.g., button or text) displayed by control interface 151. The image data is acquired by the camera 152, while the true color data is acquired by the color sensor unit 154. Control interface 151 may then send the acquired image data and true color data to server 101 for processing.

At 306, image processing module 122 integrates the image data and the true color data to generate normalized true color data. The number of pixels in the true color data (e.g., less than 20 pixels) may be much less than the number of pixels in the image data (e.g., 5 megapixels). The image processing module 122 may interpolate all pixels of the true color data within the isolated region of interest and return normalized true color data for accurate appearance analysis.

At 308, image processing module 122 maps the normalized true color data to device-independent color image data. The normalized true color data referenced to the device-independent color values may then be encrypted and stored in database 124 or any other secure storage.

In some implementations, the device-independent color values comprise CIE L*a*b* (or CIELAB) color values. CIE L*a*b* (CIELAB) is the most complete color space specified by the International Commission on Illumination. It describes all the colors visible to the human eye and was created to serve as a device-independent model to be used as a reference. The three coordinates of CIELAB represent the lightness of the color (L*=0 yields black and L*=100 indicates diffuse white; specular white may be higher), its position between red/magenta and green (a*, negative values indicate green while positive values indicate magenta) and its position between yellow and blue (b*, negative values indicate blue and positive values indicate yellow). The nonlinear relations for L*, a*, and b* are intended to mimic the nonlinear response of the eye. Furthermore, uniform changes of components in the L*a*b* color space aim to correspond to uniform changes in perceived color, so the relative perceptual differences between any two colors in L*a*b* can be approximated by treating each color as a point in a three-dimensional space (with three components: L*, a*, b*) and taking the Euclidean distance between them.

There is no simple formula for mapping normalized RGB true color values to CIELAB, because the RGB color models are device-dependent. In some implementations, image processing module 122 maps the normalized colors from tristimulus (or RGB) values to a specific absolute color space (e.g., sRGB or Adobe RGB) values and then finally to CIELAB reference color values. For example, sRGB is a standard RGB color space which uses the ITU-R BT.709 primaries, the same as are used in studio monitors and high-definition televisions (HDTV), and a transfer function (gamma curve) typical of cathode ray tubes (CRTs) that allows it to be directly displayed on typical CRT monitors. It should be appreciated that other types of color models may also be used.

Figure 4:
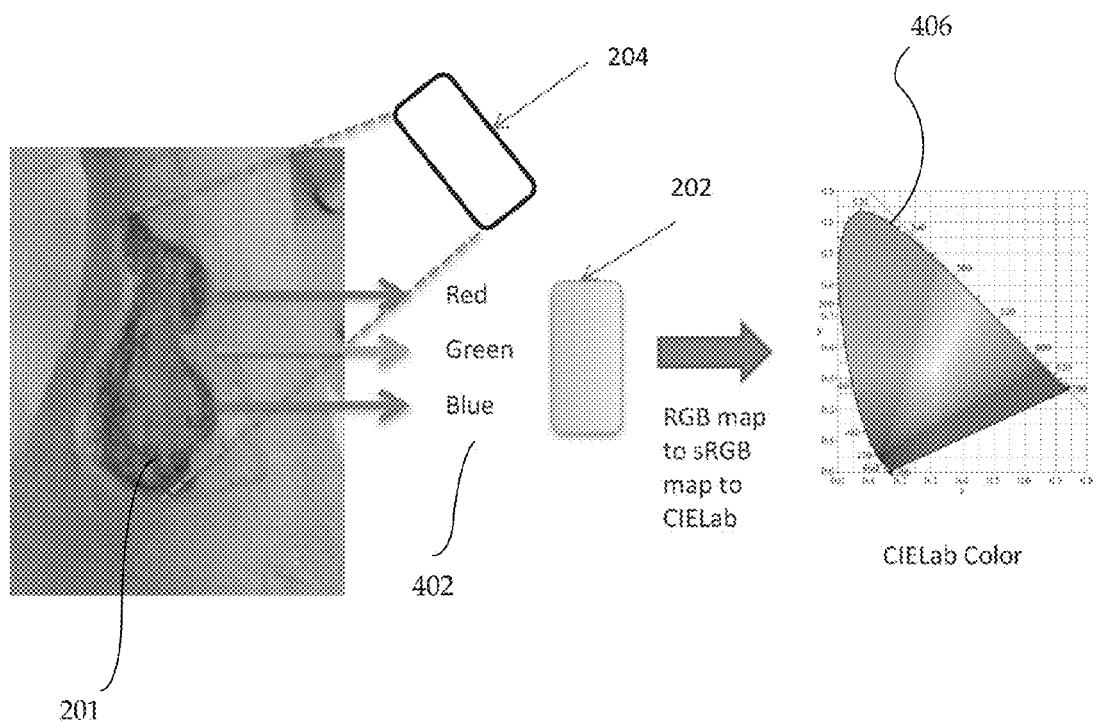
FIG. 4 illustrates an exemplary mapping of color values.

FIG. 4 illustrates an exemplary mapping of color values. More particularly, the tristimulus (or RGB) color values 402 acquired by the color sensor 202 are transformed to a sRGB color space before mapping to CIELAB 406. This adjustment may be device-dependent, but the resulting data from the transform will be device-independent.

Returning to FIG. 3, at 310, image processing module 122 sends a recommendation based on device-independent color image data. The recommendation may be provided by, for example, a user (e.g., physician, nurse or other caregiver) via client system 160. For example, the user may remotely review the device-independent color image displayed view user interface 162 and provide recommendations for wound management (e.g., treatment, clinic visits, etc.). The device-independent color image data advantageously provides a true color representation of the wound to enable correct assessment. In some implementations, the image processing module 122 provides additional information to support the user assessment. For example, such additional information may include quantitative information derived from the color image data, such as dimension measurements (e.g., length, width, depth, etc.) of the wound or other region of interest.

Although the one or more above-described implementations have been described in language specific to structural features and/or methodological steps, it is to be understood that other implementations may be practiced without the specific features or steps described. Rather, the specific features and steps are disclosed as preferred forms of one or more implementations.

The invention claimed is:

1. A system for remote monitoring, comprising:
a mobile device including a camera that acquires image data of a region of interest;
a color sensor attached to the mobile device by a connector inserted into an input channel of the mobile device, wherein the color sensor acquires true color data of the region of interest;
a computer system that integrates the image data and the true color data by interpolating pixels of the true color data within the region of interest to generate normalized true color data; and
the computer system that receives the image data and the true color data of the region of interest and maps the image data and the true color data to device-independent color image data for assessment by a user.

2. The system of claim 1 wherein the region of interest comprises a wound.

3. The system of claim 1 wherein the mobile device comprises a personal data assistant.

4. The system of claim 1 wherein the true color data comprises red green blue (RGB) values.

5. The system of claim 1 wherein the color sensor comprises a true color sensor and a light source.

6. The system of claim 1 wherein the computer system comprises a cloud service provider.

7. The system of claim 1 wherein the device-independent color image data comprises CIELAB values.

8. A method for remote monitoring, comprising:
receiving, by a computer system from a mobile device, image data and corresponding true color data of a region of interest, wherein number of pixels in the true color data is less than number of pixels in the image data;
integrating, by the computer system, the image data and the true color data by interpolating pixels of the true color data within the region of interest to generate normalized true color data;
mapping, by the computer system, the normalized true color data to device-independent color image data; and
sending, by the computer system to the mobile device, a recommendation based on the device-independent color image data.

9. The method of claim 8 further comprising acquiring, by a color sensor unit communicatively coupled to the mobile device, the true color data of the region of interest.

10. The method of claim 8 wherein receiving the true color data comprises receiving red, green and blue (RGB) color values.

11. The method of claim 8 wherein mapping the normalized true color data to the device-independent color image data comprises mapping red, green and blue (RGB) color values to CIELAB color values.

12. The method of claim 11 wherein mapping the RGB color values to the CIELAB color values comprises mapping the RGB color values to sRGB color values and mapping the sRGB color values to the CIELAB color values.

13. The method of claim 8 wherein sending the recommendation based on the device-independent color image data comprises sending a recommendation for wound management provided by a caregiver reviewing the device-independent color image data.

14. A non-transitory computer-readable medium having stored thereon program code, the program code executable by a computer to:
receive image data and corresponding true color data of a region of interest, wherein number of pixels in the true color data is less than number of pixels in the image data;
integrate the image data and the true color data by interpolating pixels of the true color data within the region of interest to generate normalized true color data;
map the normalized true color data to device-independent color image data; and
send a recommendation based on the device-independent color image data.

15. The computer-readable medium of claim 14 wherein the program code is executable by the computer to receive the true color data by receiving red, green and blue (RGB) color values.

16. The computer-readable medium of claim 14 wherein the program code is executable by the computer to map the normalized true color data to the device-independent color image data by mapping red, green and blue (RGB) color values to CIELAB color values.

17. The computer-readable medium of claim 16 wherein the program code is executable by the computer to map the RGB color values to the CIELAB color values by mapping the RGB color values to sRGB color values and mapping the sRGB color values to the CIELAB color values.

18. The computer-readable medium of claim 14 wherein the program code is executable by the computer to send the recommendation based on the device-independent color image data by sending a recommendation for wound management provided by a caregiver reviewing the device-independent color image data.

* * * * *